United States Patent
Mallat et al.

(10) Patent No.: US 12,144,859 B2
(45) Date of Patent: Nov. 19, 2024

(54) B CELL DEPLETING AGENT FOR THE TREATMENT OF ATHEROSCLEROSIS

(71) Applicants: Ziad Mallat, Paris (FR); Hafid Ait-Oufella, Paris (FR); Alain Tedgui, Paris (FR); Thomas Tedder, Durham, NC (US)

(72) Inventors: Ziad Mallat, Paris (FR); Hafid Ait-Oufella, Paris (FR); Alain Tedgui, Paris (FR); Thomas Tedder, Durham, NC (US)

(73) Assignees: Institut National De La Santa Et De La Recherche Medicale (Inserm), Paris (FR); Duke University, Durham, NC (US); Assistance Publique-Hôpitaux De Paris (APHP), Paris (FR)

( * ) Notice: Subject to any disclaimer, the term of this patent is extended or adjusted under 35 U.S.C. 154(b) by 57 days.

(21) Appl. No.: 16/902,518

(22) Filed: Jun. 16, 2020

(65) Prior Publication Data
US 2020/0376118 A1 Dec. 3, 2020

Related U.S. Application Data

(63) Continuation of application No. 16/505,788, filed on Jul. 9, 2019, now abandoned, which is a continuation of application No. 13/790,771, filed on Mar. 8, 2013, now abandoned, which is a continuation of application No. 13/143,440, filed as application No. PCT/EP2010/050048 on Jan. 5, 2010, now abandoned.

(30) Foreign Application Priority Data

Jan. 6, 2009 (EP) .................................. 09290005
Jan. 7, 2009 (EP) .................................. 09305013

(51) Int. Cl.
| | |
|---|---|
| A61K 39/395 | (2006.01) |
| A61K 39/00 | (2006.01) |
| A61K 47/68 | (2017.01) |
| C07K 16/24 | (2006.01) |
| C07K 16/28 | (2006.01) |

(52) U.S. Cl.
CPC ...... *A61K 39/3955* (2013.01); *A61K 47/6849* (2017.08); *C07K 16/244* (2013.01); *C07K 16/2887* (2013.01); *A61K 2039/505* (2013.01); *C07K 2317/24* (2013.01)

(58) Field of Classification Search
None
See application file for complete search history.

(56) References Cited

U.S. PATENT DOCUMENTS

| | | | |
|---|---|---|---|
| 2008/0095771 A1* | 4/2008 | Barron | A61P 17/06 424/133.1 |
| 2010/0093636 A1* | 4/2010 | Schultz | A61P 15/00 530/326 |

OTHER PUBLICATIONS

White et al. 'Acute myocardial infarction.' Lancet 372:570-584, 2008.*
Chan et al. 'Obligatory Role for B Cells in the Development of Angiotensin II—Dependent Hypertension.' Hypertension. 2015;66: 1023-1033. DOI: 10.1161/HYPERTENSIONAHA.115.05779.*
Rubinfeld 2023.*

* cited by examiner

*Primary Examiner* — Nora M Rooney
(74) *Attorney, Agent, or Firm* — WC&F IP

(57) ABSTRACT

The present invention relates to the prevention or treatment of atherosclerosis, in particular to a B cell depleting agent for the prevention or treatment of atherosclerosis.

10 Claims, 15 Drawing Sheets

B CELL DEPLETING AGENT FOR THE TREATMENT OF ATHEROSCLEROSIS

FIELD OF THE INVENTION

Figure 1:
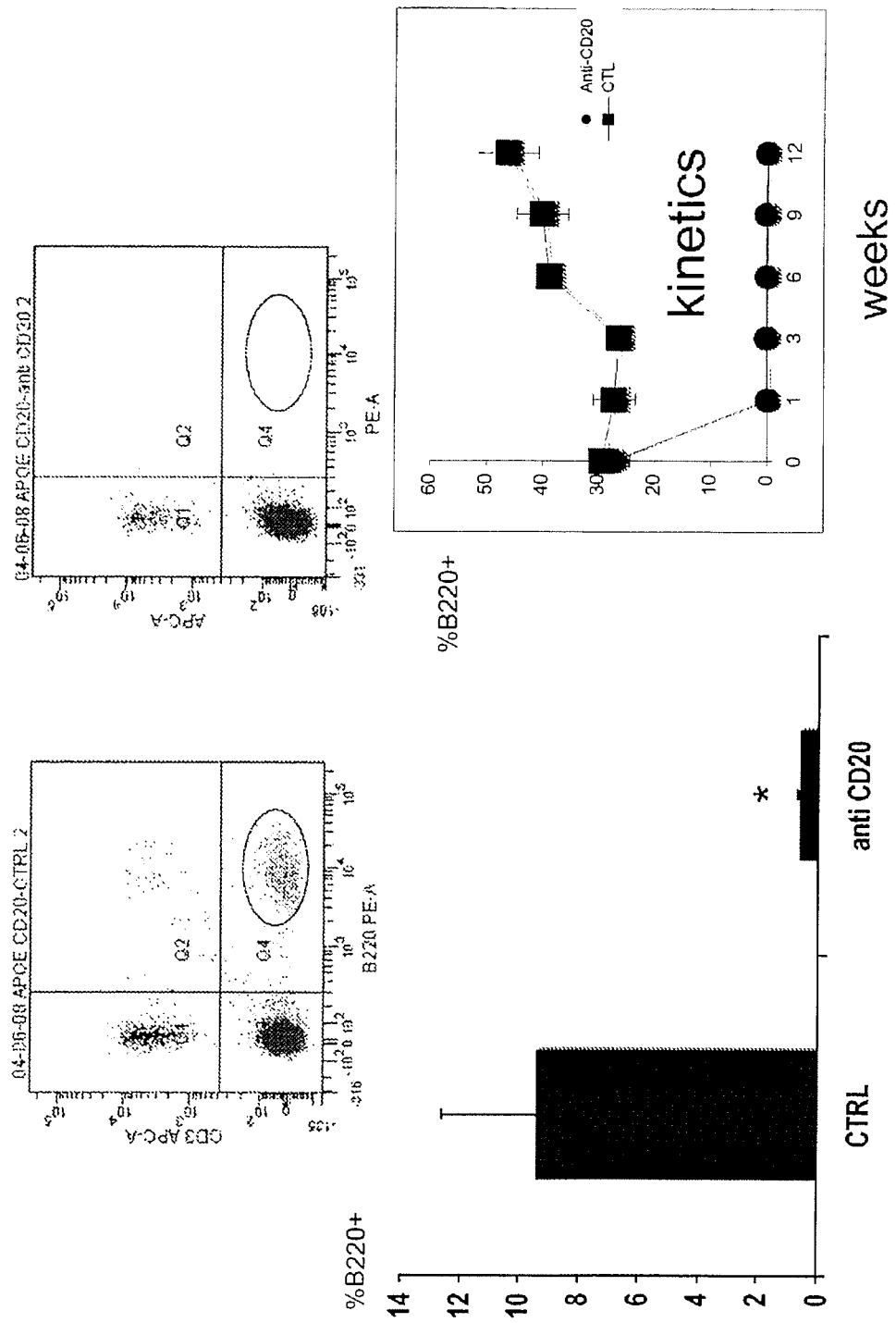

The present invention relates to the prevention or treatment of atherosclerosis, in particular to a B cell depleting agent for the prevention or treatment of atherosclerosis.

BACKGROUND OF THE INVENTION

Atherosclerosis is the most common cause of death in western societies and is predicted to become the leading cause of cardiovascular disease in the world within two decades.

Atherosclerosis contributes to the development of atherosclerotic vascular diseases (AVD) which may affect the coronary arteries (causing ischaemic heart disease), the cerebral circulation (causing cerebrovascular disease), the aorta (producing aneurysms that are prone to thrombosis and rupture) and peripheral blood vessels, typically the legs (causing peripheral vascular disease and intermittent claudication). Ischaemic heart disease (IHD) includes angina (chest pain caused by insufficient blood supply to cardiac muscle) and myocardial infarction (death of cardiac muscle) and cerebrovascular disease includes stroke and transient ischaemic attacks. One in three men and one in four women will die from IHD and the death rate for IHD was 58 per 100,000 in 1990.

Atherosclerotic plaques begin as fatty streaks underlying the endothelium of large arteries. Recruitment of macrophages and their subsequent uptake of LDL derived cholesterol are the major cellular events contributing to fatty streak formation. Many lines of evidence suggest that oxidative or non-oxidative modifications in the lipid and apolipoprotein B (apo B) components of LDL drive the initial formation of fatty streaks. The specific properties of oxidized LDL (oxLDL), usually studied following oxidation of native LDL in vitro, depend on the extent of modification. This can range from "minimal" modification (mmLDL) wherein the LDL particle can still be recognized by LDL receptors, to extensive oxidation wherein the apoB component is fragmented and lysine residues are covalently modified with reactive breakdown products of oxidized lipids. Such particles are not bound by the LDL receptor but rather by so called scavenger receptors expressed on macrophages and smooth muscle cells. A large number of proinflammatory and proatherogenic properties have been ascribed to mmLDL and oxLDL and their components. For instance, lysophosphatidylcholine or oxidized phospholipids increase monocyte's adhesion, monocyte and T cell chemotaxis and can induce proinflammatory gene expression. Although the recruitment of monocytes to the arterial wall and their subsequent differentiation into macrophages may initially serve a function by removing cytotoxic and proinflammatory oxLDL particles or apoptotic cells, progressive accumulation of macrophages and their uptake of oxLDL ultimately leads to development of atherosclerotic lesions.

The transition from the relatively simple fatty streak to the more complex plaque is characterized by the migration of smooth muscle cells from the medial layer of the artery wall to the internal elastic lamina and to intimal or subendothelial space, or by recruitment of smooth muscle cell progenitors. Intimal smooth muscle cells may proliferate and take up modified lipoproteins, thus contributing to foam cell formation, and synthesize extracellular matrix proteins that lead to the development of the fibrous cap. Thus, the advanced atherosclerotic plaque is schematically divided into two portions: the fibrous cap making up the surface layer and a lipid core making up the deep layer. This extra-cellular matrix (ECM) is composed of vastly different macromolecules including collagen, elastin, glycoproteins and proteoglycans. Large amounts of ECM are deposited in the fibrous cap, with the strength of the plaque maintained, whereas in the lipid core in addition to lipid deposition, ECM degradation is enhanced, leading to increased tissue fragility. This plaque fragility gives rise to plaque vulnerability in turn becoming a cause of plaque rupture.

This phase of plaque development is influenced by interactions between monocyte/macrophages and T cells that result in a broad range of cellular and humoral responses and the acquisition of many features of a chronic inflammatory state. Significant cross talk appears to occur among the cellular elements of developing lesions. Lesional T cells appear to be activated and express both Th1 and Th2 cytokines). Similarly, macrophages, endothelial cells and smooth muscle cells appear to be activated based on their expression of MHC class II molecules and numerous inflammatory products such as TNF, IL-6 and MCP 1.

So, there is a recognized and permanent need in the art for new reliable methods for treating atherosclerosis.

An existing approach for the treatment of atherosclerosis is based on evidence that the Th1 and Th2 pathways appear to play a key role. Thus immunomodulatory treatment that promotes regulatory immunity can represent an attractive tool for treating and/or preventing atherosclerosis. This might be accomplished by promoting regulatory T cell (Treg) generation such as Tr1 cells, CD4+CD25+cells or Th3 cells. In that context, it has been show that naturally arising CD4(+)CD25(+) regulatory T cells, which actively maintain immunological tolerance to self and nonself antigens, are powerful inhibitors of atherosclerosis in several mouse models.

On the other hand, a recent study suggests that B cells deficiency increases atherosclerosis in a mouse model (Major al. 2002). Another recent study has shown that protection against atherosclerosis was conferred by B cells (Caligiuri et al., 2002). Accordingly, the prior art suggests that depletion of B cells is not a promising method for the treatment of atherosclerosis, contrary to what is disclosed, but not demonstrated, in the following patent applications US2004/202658, US2005/186206, US2008/260641, WO2007/053661 and US2004/167619.

SUMMARY OF THE INVENTION

The present invention relates to a B cell depleting agent for the treatment or prevention of atherosclerosis.

The present invention also relates to a pharmaceutical composition for the treatment or prevention of atherosclerosis.

DETAILED DESCRIPTION OF THE INVENTION

The inventors have demonstrated that administration of a B cell depleting agent (i.e. an anti-CD20 antibody) allows significant reduction of atherosclerotic plaque size in a mouse model.

B cell-dependent responses are involved in the pathogenesis of (auto)-immune disorders and B cell depletion significantly reduces the burden of several immune-mediated diseases. However, B cell activation has been until now associated with a protection against atherosclerosis (Caligiuri et al., 2002; Major et al., 2002; Binder et al., 2004; Miller et al., 2008), suggesting that B cell depleting therapies would enhance cardiovascular risk.

Here, inventors unexpectedly show that mature B cell depletion using a CD20 monoclonal antibody induces a significant reduction of atherosclerosis in various mouse models of the disease. This treatment preserves the production of natural and potentially protective anti-oxidized low-density lipoprotein (oxLDL) IgM autoantibodies over IgG type anti-oxLDL antibodies, and markedly reduces pathogenic T cell activation. The atheroprotective mechanisms of B cell depletion involve a switch of the immune response towards diminished T cell-derived interferon-gamma secretion and enhanced production of interleukin-17, whose neutralization abrogates CD20 antibody-mediated atheroprotection.

These results challenge the current paradigm that B cell activation play an overall protective role in atherogenesis, identify new anti-atherogenic strategies based on B cell modulation, and suggest that patients currently treated with B cells depleting agents such as CD20 antibodies for other immune-mediated diseases might also benefit from a reduction of cardiovascular risk through limitation of atherosclerotic lesion development or inflammation.

Inventors also showed that B cell depletion is beneficial in myocardial infarction.

Definitions

The term "B cell" has its general meaning in the art. B cells are lymphocytes that play a large role in the humoral immune response (as opposed to the cell-mediated immune response, which is governed by T cells).

A "B cell depleting agent" is a molecule which depletes or destroys B cells in a patient and/or interferes with one or more B cell functions, e.g. by reducing or preventing a humoral response elicited by the B cell. The B cell depleting agent preferably binds to a B cell surface marker. The B cell depleting agent preferably is able to deplete B cells (i.e. reduce circulating B cell levels) in a patient treated therewith. Such depletion may be achieved via various mechanisms such antibody-dependent cell mediated cytotoxicity (ADCC) and/or complement dependent cytotoxicity (CDC), inhibition of B cell proliferation and/or induction of B cell death (e.g. via apoptosis). B cell depleting agents include but are not limited to antibodies, synthetic or native sequence peptides and small molecule antagonists which preferably bind to the B cell surface marker, optionally conjugated with or fused to a cytotoxic agent. The preferred B cell depleting agent comprises an antibody, more preferably a B cell depleting antibody.

In a preferred embodiment, the B cell depleting agent has not the capability to deplete plasma cells. In another preferred embodiment, the B cell depleting agent has not the capability to deplete B10 cells (or Breg cells). In another preferred embodiment, the B cell depleting agent has not the capability to deplete B1 cells. Accordingly, in a particular preferred embodiment the B cell depleting agent has not the capability to deplete plasma cells and B10 cells. Accordingly, in a particular preferred embodiment the B cell depleting agent has not the capability to deplete plasma cells, B10 cells and B1 cells.

"Complement dependent cytotoxicity" or "CDC" refers to the lysis of a target cell in the presence of complement. Activation of the classical complement pathway is initiated by the binding of the first component of the complement system to antibodies which are bound to their cognate antigen. To assess complement activation, a CDC assay, e.g. as described in Gazzano-Santoro et al. (1997) may be performed.

"Antibody-dependent cell-mediated cytotoxicity" or "ADCC" refers to a form of cytotoxicity in which secreted antibodies bound onto Fc receptors (FcRs) present on certain cytotoxic cells (e.g. Natural Killer (NK) cells, neutrophils, monocytes and macrophages) enable these cytotoxic effector cells to bind specifically to an antigen-bearing target cell and subsequently kill the target cell. To assess ADCC activity of a molecule of interest, an in vitro ADCC assay, such as that described in U.S. Pat. No. 5,500,362 or 5,821,337 may be performed.

A "B cell surface marker" or "B cell target" or "B cell antigen" herein is an antigen expressed on the surface of a B cell which can be targeted with a B cell depleting agent which binds thereto. Exemplary B cell surface markers include but are not limited to the CD10, CD19, CD20, CD21, CD22, CD23, CD24, CD37, CD53, CD72, CD73, CD74, CDw75, CDw76, CD77, CDw78, CD79a, CD79b, CD80, CD81, CD82, CD83, CDw84, CD85 and CD86 leukocyte surface markers. The B cell surface marker of particular interest is preferentially expressed on B cells compared to other non-B cell tissues of a mammal and may be expressed on both precursor B cells and mature B cells. In one embodiment, the marker is one like CD20 or CD19, which is found on B cells throughout differentiation of the lineage from the stem cell stage up to a point just prior to terminal differentiation into plasma cells.

A "CD20" antigen is a 35 kDa, non-glycosylated phosphoprotein found on the surface of greater than 90% of B cells from peripheral blood or lymphoid organs. CD20 is expressed during early pre-B cell development and remains until plasma cell differentiation. CD20 is present on both normal B cells as well as malignant B cells. Other names for CD20 in the literature include "B-lymphocyte-restricted antigen" and "Bp35". The CD20 antigen is described in, e.g., Clark et al. PNAS (USA) 82:1766 (1985).

According to the present invention, "antibody" or "immunoglobulin" have the same meaning, and will be used equally in the present invention. The term "antibody" as used herein refers to immunoglobulin molecules and immunologically active portions of immunoglobulin molecules, i.e., molecules that contain an antigen binding site that immunospecifically binds an antigen. As such, the term antibody encompasses not only whole antibody molecules, but also antibody fragments as well as variants (including derivatives) of antibodies and antibody fragments. In natural antibodies, two heavy chains are linked to each other by disulfide bonds and each heavy chain is linked to a light chain by a disulfide bond. There are two types of light chain, lambda (l) and kappa (k). There are five main heavy chain classes (or isotypes) which determine the functional activity of an antibody molecule: IgM, IgD, IgG, IgA and IgE. Each chain contains distinct sequence domains. The light chain includes two domains, a variable domain (VL) and a constant domain (CL). The heavy chain includes four domains, a variable domain (VH) and three constant domains (CH1, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, trans-placental mobility, complement binding, and binding to Fc receptors (FcR). The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from non-hypervariable or framework regions (FR) influence the overall domain structure and hence the combining site. Complementarity Determining Regions or CDRs refer to amino acid sequences which together define the binding affinity and specificity of the natural Fv region of a native immunoglobulin binding site. The light and heavy chains of an immunoglobulin each have three CDRs, designated L-CDR1, L-CDR2, L-CDR3 and H-CDR1, H-CDR2, H-CDR3, respectively. An antigen-binding site, therefore, includes six CDRs, comprising the CDR set from each of a heavy and a light chain V region. Framework Regions (FRs) refer to amino acid sequences interposed between CDRs.

The term "chimeric antibody" refers to an antibody which comprises a VH domain and a VL domain of an antibody of the invention, and a CH domain and a CL domain of a human antibody.

According to the invention, the term "humanized antibody" refers to an antibody having variable region framework and constant regions from a human antibody but retains the CDRs of the antibody of the invention.

The term "Fab" denotes an antibody fragment having a molecular weight of about 50,000 and antigen binding activity, in which about a half of the N-terminal side of H chain and the entire L chain, among fragments obtained by treating IgG with a protease, papaine, are bound together through a disulfide bond.

The term "F(ab')2" refers to an antibody fragment having a molecular weight of about 100,000 and antigen binding activity, which is slightly larger than the Fab bound via a disulfide bond of the hinge region, among fragments obtained by treating IgG with a protease, pepsin.

The term "Fab'" refers to an antibody fragment having a molecular weight of about 50,000 and antigen binding activity, which is obtained by cutting a disulfide bond of the hinge region of the F(ab')2.

A single chain Fv ("scFv") polypeptide is a covalently linked VH::VL heterodimer which is usually expressed from a gene fusion including VH and VL encoding genes linked by a peptide-encoding linker. "dsFv" is a VH::VL heterodimer stabilised by a disulfide bond. Divalent and multivalent antibody fragments can form either spontaneously by association of monovalent scFvs, or can be generated by coupling monovalent scFvs by a peptide linker, such as divalent sc(Fv)2.

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites.

"B cell depleting antibodies" are defined as those antibodies which bind to a B cell surface marker on the surface of B cells and mediate their destruction or depletion when they bind to said cell surface marker. The term includes antibody fragments. Such antibodies include, but are not limited to, anti-CD20, anti-CD19, anti-CD22, anti-CD21, anti-CD23, anti-CD28, anti-CD37, anti-CD40, anti-CD52 antibodies. An example of an anti-CD20 antibody is RITUXAN® (rituximab). B cell depleting antibodies also include antibodies that destroy B cells via other mechanisms. For example, these include radiolabeled antibodies that facilitate the destruction of B cells by binding to the B cell surface and delivering a lethal dose of radiation. These include 131 I-Lym-1 (anti-HLA-D), 131 I-tositumomab (BEXXAR®), ibritumomab tiuxetan (Y-90, In-I 11 ZEVALIN®) and 90 Y-epratuzumab.

In the context of the invention, the term "treating" or "treatment", as used herein, means reversing, alleviating, or inhibiting the progress of the disorder or condition to which such term applies, or one or more symptoms of such disorder or condition. A "therapeutically effective amount" is intended for a minimal amount of active agent which is necessary to impart therapeutic benefit to a subject. For example, a "therapeutically effective amount" to a patient is such an amount which induces, ameliorates or otherwise causes an improvement in the pathological symptoms, disease progression or physiological conditions associated with or resistance to succumbing to a disorder.

In its broadest meaning, the term "preventing" or "prevention" refers to preventing the disease or condition from occurring in a subject which has not yet been diagnosed as having it.

The term "patient" refers to any subject (preferably human) afflicted with or susceptible to be afflicted with atherosclerosis.

"Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

Methods of Treatment

The present invention relates to a method for preventing or treating atherosclerosis in a patient in need thereof comprising the step of depleting the B cells population of said patient.

More particularly, the present invention relates to a method for preventing or treating atherosclerosis in a patient in need thereof comprising the step of administrating said patient with a B cell depleting agent.

The method according to the present invention can be supplied to a patient, which has been diagnosed as presenting one of the following coronary disorders:
  asymptomatic coronary artery coronary diseases with silent ischemia or without ischemia;
  chronic ischemic disorders without myocardial necrosis, such as stable or effort angina pectoris;
  acute ischemic disorders without myocardial necrosis, such as unstable angina pectoris;
  ischemic disorders with myocardial necrosis, such as ST segment elevation myocardial infarction or non-ST segment elevation myocardial infarction.

Indeed, said pathologies are atherosclerosis complications and are thus considered as indicative of atherosclerosis.

A further aspect of the invention relates to a method for preventing or treating a vascular or coronary disorder in a patient in need thereof comprising the step of depleting the B cells population of said patient.

More particularly, the invention relates to a method for preventing or treating a vascular or coronary disorder comprising the step of administrating a patient in need thereof with a B cell depleting agent.

In a particular embodiment, said coronary disorder or vascular disorders is selected from the group consisting of atherosclerotic vascular disease, such as aneurysm or stroke, asymptomatic coronary artery coronary diseases, chronic ischemic disorders without myocardial necrosis, such as stable or effort angina pectoris; acute ischemic disorders without myocardial necrosis, such as unstable angina pectoris; and ischemic disorders such as myocardial infarction.

In a particular embodiment, the invention relates to a method for preventing or treating myocardial infarction in a patient in need thereof comprising the step of depleting the B cells population of said patient.

More particularly, the invention relates to a method for preventing or treating myocardial infarction comprising the step of administrating a patient in need thereof with a B cell depleting agent.

In another particular embodiment, the invention relates to a method for preventing or treating aneurysm in a patient in need thereof comprising the step of depleting the B cells population of said patient.

More particularly, the invention relates to a method for preventing or treating aneurysm comprising the step of administrating a patient in need thereof with a B cell depleting agent.

In particular embodiment the B cell depleting agent may consist in a B cell depleting antibody.

Antibodies directed against a B cell surface marker can be raised according to known methods by administering the appropriate antigen or epitope to a host animal selected, e.g., from pigs, cows, horses, rabbits, goats, sheep, and mice, among others. Various adjuvants known in the art can be used to enhance antibody production. Although antibodies useful in practicing the invention can be polyclonal, monoclonal antibodies are preferred.

Monoclonal antibodies can be prepared and isolated using any technique that provides for the production of antibody molecules by continuous cell lines in culture. Techniques for production and isolation include but are not limited to the hybridoma technique, the human B-cell hybridoma technique and the EBV-hybridoma technique. Alternatively, techniques described for the production of single chain antibodies (see, e.g., U.S. Pat. No. 4,946,778) can be adapted to produce single chain antibodies against a B cell surface marker. Useful antibodies according to the invention also include antibody fragments including but not limited to F(ab')2 fragments, which can be generated by pepsin digestion of an intact antibody molecule, and Fab fragments, which can be generated by reducing the disulfide bridges of the F(ab')2 fragments. Alternatively, Fab and/or scFv expression libraries can be constructed to allow rapid identification of fragments having the desired specificity to the B cell surface marker.

Humanized antibodies and antibody fragments therefrom can also be prepared according to known techniques. "Humanized antibodies" are forms of non-human (e.g., rodent) chimeric antibodies that contain minimal sequence derived from non-human immunoglobulin. For the most part, humanized antibodies are human immunoglobulins (recipient antibody) in which residues from a hypervariable region (CDRs) of the recipient are replaced by residues from a hypervariable region of a non-human species (donor antibody) such as mouse, rat, rabbit or nonhuman primate having the desired specificity, affinity and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. Methods for making humanized antibodies are described, for example, by Winter (U.S. Pat. No. 5,225,539) and Boss (Celltech, U.S. Pat. No. 4,816,397).

Then after raising antibodies directed against a B cell surface marker as above described, the skilled man in the art can easily select those that deplete B cells, for example those that deplete B cells via antibody-dependent cell mediated cytotoxicity (ADCC), complement dependent cytotoxicity (CDC), inhibition of B cell proliferation or induction of B cell death (e.g. via apoptosis).

In a particular embodiment, the B cell depleting antibody may consist in an antibody directed against a B cell surface marker which is conjugated to a cytotoxic agent or a growth inhibitory agent.

Accordingly the invention contemplates the use of immunoconjugates comprising an antibody against a B cell surface marker conjugated to a cytotoxic agent or a growth inhibitory agent.

A "growth inhibitory agent" when used herein refers to a compound or composition which inhibits growth of a cell, especially B cell, either in vitro or in vivo. Examples of growth inhibitory agents include agents that block cell cycle progression, such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, and 5-fluorouracil.

The term "cytotoxic agent" as used herein refers to a substance that inhibits or prevents the function of cells and/or causes destruction of cells. The term is intended to include radioactive isotopes (e.g. At211, I131, I125, Y90, Re186, Re188, Sm153, Bi212, P32, and radioactive isotopes of Lu), chemotherapeutic agents, e.g., methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, e.g., gelonin, ricin, saporin, and the various antitumor or anticancer agents disclosed below. Other cytotoxic agents are described below. A tumoricidal agent causes destruction of tumor cells.

Conjugation of the antibodies of the invention with cytotoxic agents or growth inhibitory agents may be made using a variety of bifunctional protein coupling agents including but not limited to N-succinimidyl (2-pyridyldithio) propionate (SPDP), succinimidyl (N-maleimidomethyl) cyclohexane-1-carboxylate, iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6diisocyanate), and bis-active fluorine compounds (such as 1,5-difluoro-2,4-dinitrobenzene). For example, a ricin immunotoxin can be prepared as described in Vitetta et al (1987). Carbon labeled 1-isothiocyanatobenzyl methyldiethylene triaminepentaacetic acid (MX-DTPA) is an exemplary chelating agent for conjugation of radionucleotide to the antibody (WO 94/11026).

Alternatively, a fusion protein comprising the antibody and cytotoxic agent or growth inhibitory agent may be made, by recombinant techniques or peptide synthesis. The length of DNA may comprise respective regions encoding the two portions of the conjugate either adjacent one another or separated by a region encoding a linker peptide which does not destroy the desired properties of the conjugate.

In a particular embodiment, the preferred B cell surface marker is CD20.

Thus, in a preferred embodiment of the invention, B cell depleting agent is an anti-CD20 antibody.

Examples of depleting antibodies that are contemplated by the invention include antibodies which bind the CD20 antigen: "C2B8" which is "rituximab" ("RITUXAN®") (U.S. Pat. No. 5,736,137, expressly incorporated herein by reference); the yttrium-[90]-labeled 2138 murine antibody designated "Y2B8" (U.S. Pat. No. 5,736,137, expressly incorporated herein by reference); murine IgG2a "131" optionally labeled with 131I to generate the "131I-B1" antibody (BEXXAR™®) (U.S. Pat. No. 5,595,721, expressly incorporated herein by reference); murine monoclonal antibody "1F5" (Press et al. Blood 69(2): 584-591 (1987)); "chimeric 2H7" antibody (U.S. Pat. No. 5,677,180 expressly incorporated herein by reference); and monoclonal antibodies L27, G28-2, 93-1133, B-C1 or NU-B2 available from the International Leukocyte Typing Workshop (Valentine et al., In: Leukocyte Typing III (M cMichael, Ed., p. 440, Oxford University Press (1987)).

The terms "rituximab" or "RITUXAN®" herein refer to the genetically engineered chimeric murine/human monoclonal antibody directed against the CD20 antigen and designated "C2B8" in U.S. Pat. No. 5,736,137, expressly incorporated herein by reference. The antibody is an IgG, kappa immunoglobulin containing murine light and heavy chain variable region sequences and human constant region sequences. Rituximab has a binding affinity for the CD20 antigen of approximately 8.0 nM. It is commercially available, e.g. from Genentech (South San Francisco, CA).

The B cell depleting agent of the invention may be administered in the form of a pharmaceutical composition, as defined below.

Preferably, said B cell depleting agent is administered in a therapeutically effective amount.

By a "therapeutically effective amount" is meant a sufficient amount of the B cell depleting agent to treat or to prevent atherosclerosis at a reasonable benefit/risk ratio applicable to any medical treatment.

It will be understood that the total perodically usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed, the age, body weight, general health, sex and diet of the patient; the time of administration, route of administration, and rate of excretion of the specific compound employed; the duration of the treatment; drugs used in combination or coincidential with the specific polypeptide employed; and like factors well known in the medical arts. For example, it is well known within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the patient to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

Pharmaceutical Compositions

The B cell depleting agent of the invention may be combined with pharmaceutically acceptable excipients, and optionally sustained-release matrices, such as biodegradable polymers, to form therapeutic compositions.

In the pharmaceutical compositions of the present invention, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The B cell depleting agent of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active polypeptides in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion. Some variation in dosage will necessarily occur depending on the condition of the subject being treated. The person responsible for administration will, in any event, determine the appropriate dose for the individual subject.

The B cell depleting agent of the invention may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered.

In addition to the compounds of the invention formulated for parenteral administration, such as intravenous or intramuscular injection, other pharmaceutically acceptable forms include, e.g. tablets or other solids for oral administration; liposomal formulations; time release capsules; and any other form currently used.

The invention will further be illustrated in view of the following figures and examples.

FIGURES

FIG. 1: B cell depletion in the blood after 3 months of anti-murine CD20 treatment, one intraperitoneal (200 µg) injection every 3 weeks.

Figure 2:
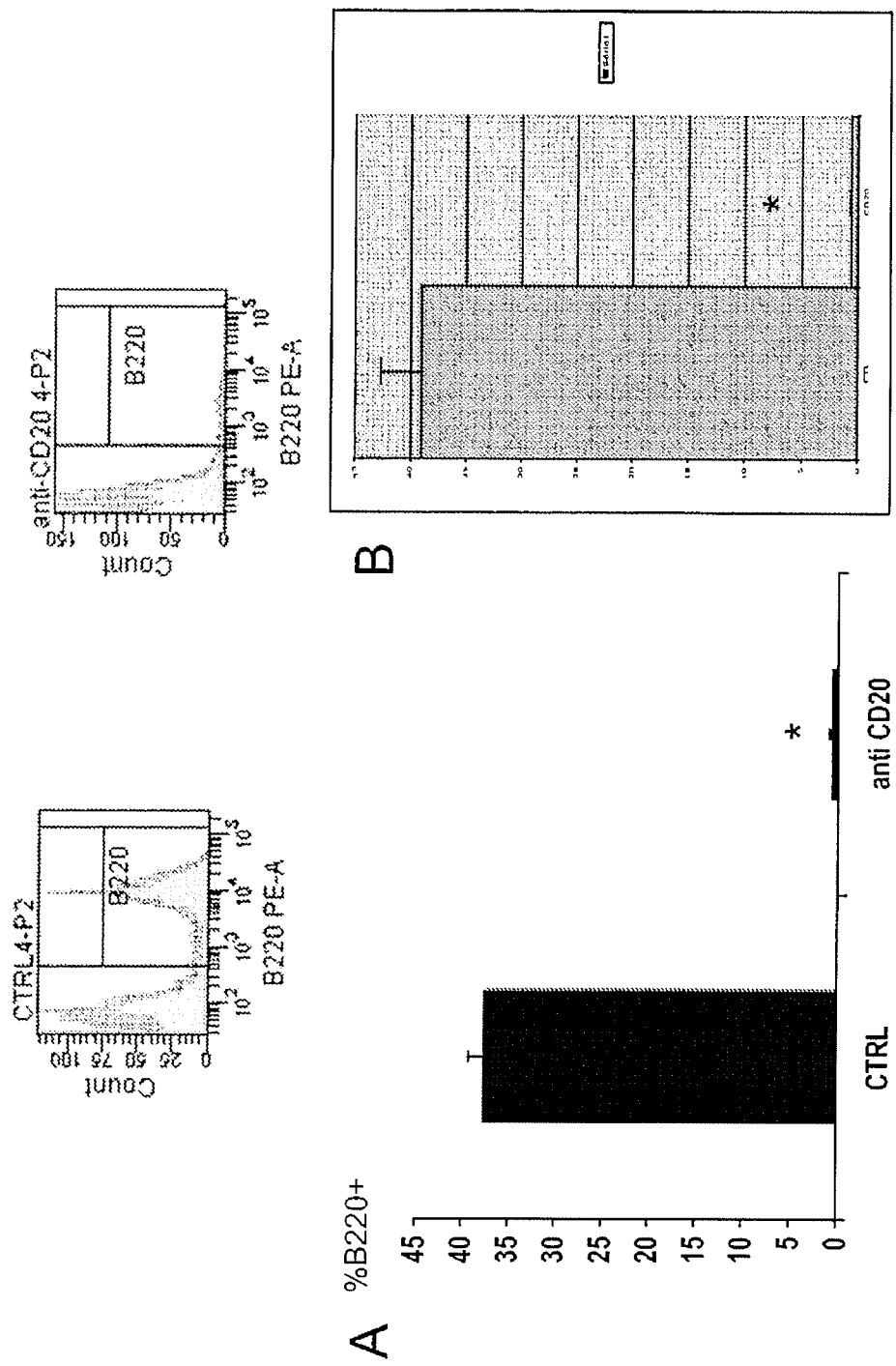

FIG. 2: B cell depletion in spleen after 3 months of anti-CD20 treatment, one intraperitoneal (200 µg) injection every 3 weeks. FIGS. 2A and 2B represent B cell depletion in 2 distinct experiments.

Figure 3:
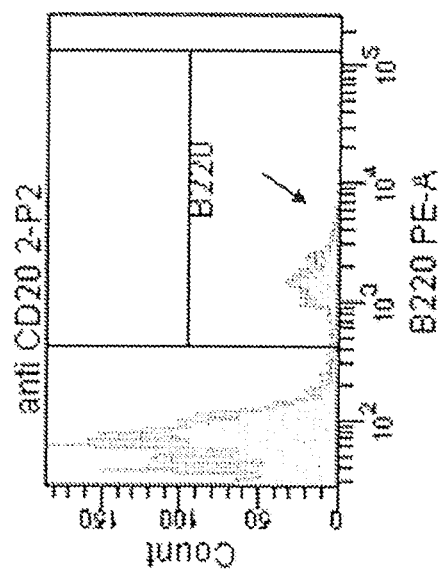
Figure 3:
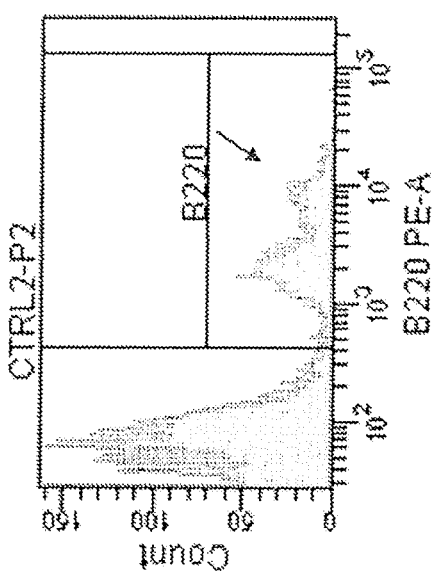

FIG. 3: B cell depletion (B220 high) in bone marrow after 3 months of anti-CD20 treatment, one intraperitoneal (200 µg) injection every 3 weeks.

Figure 4:
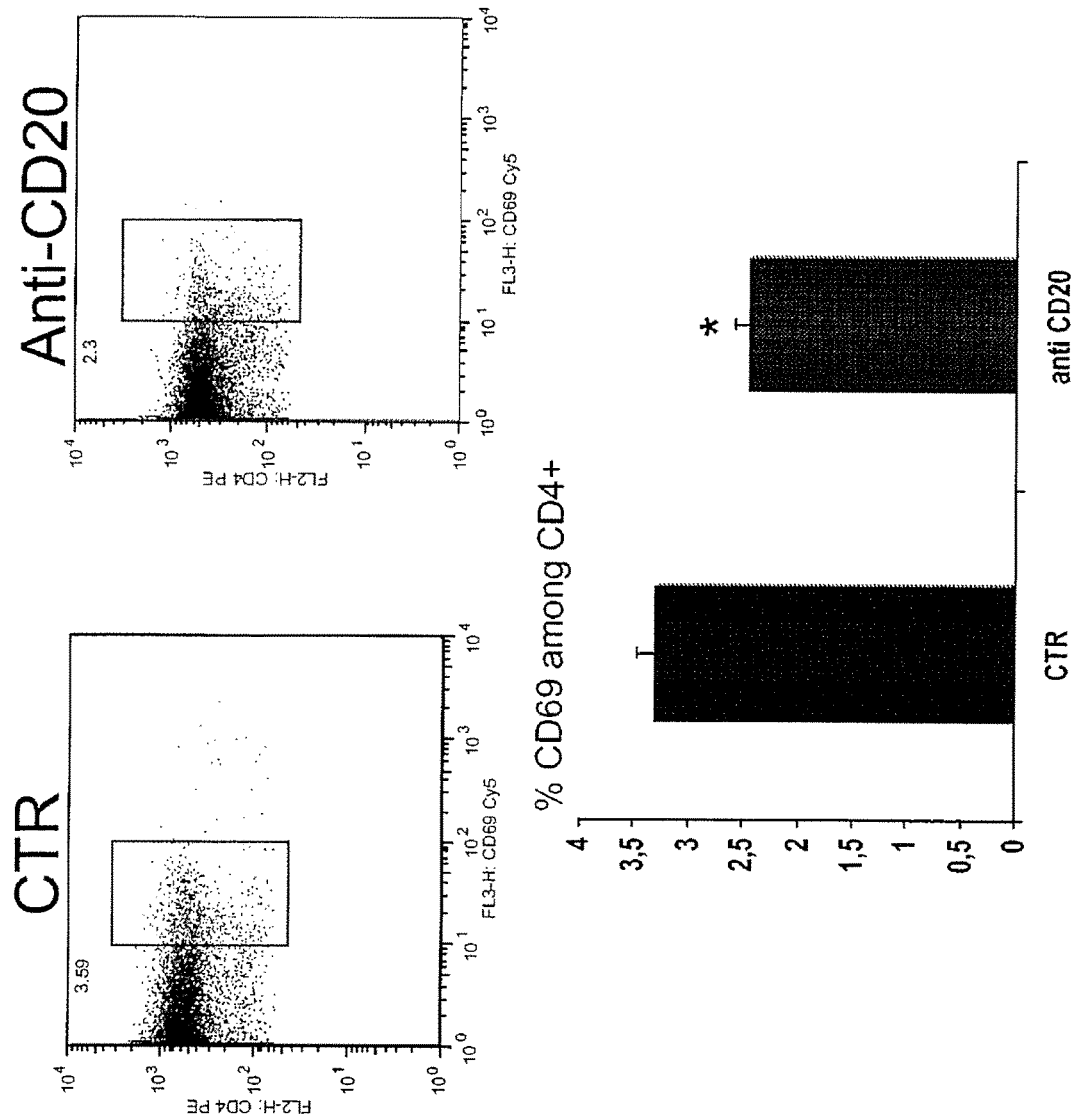

FIG. 4: B cell depletion induces a decrease of CD69 expression by splenic CD4 T cell suggesting a CD4 T cell deactivation.

Figure 5:
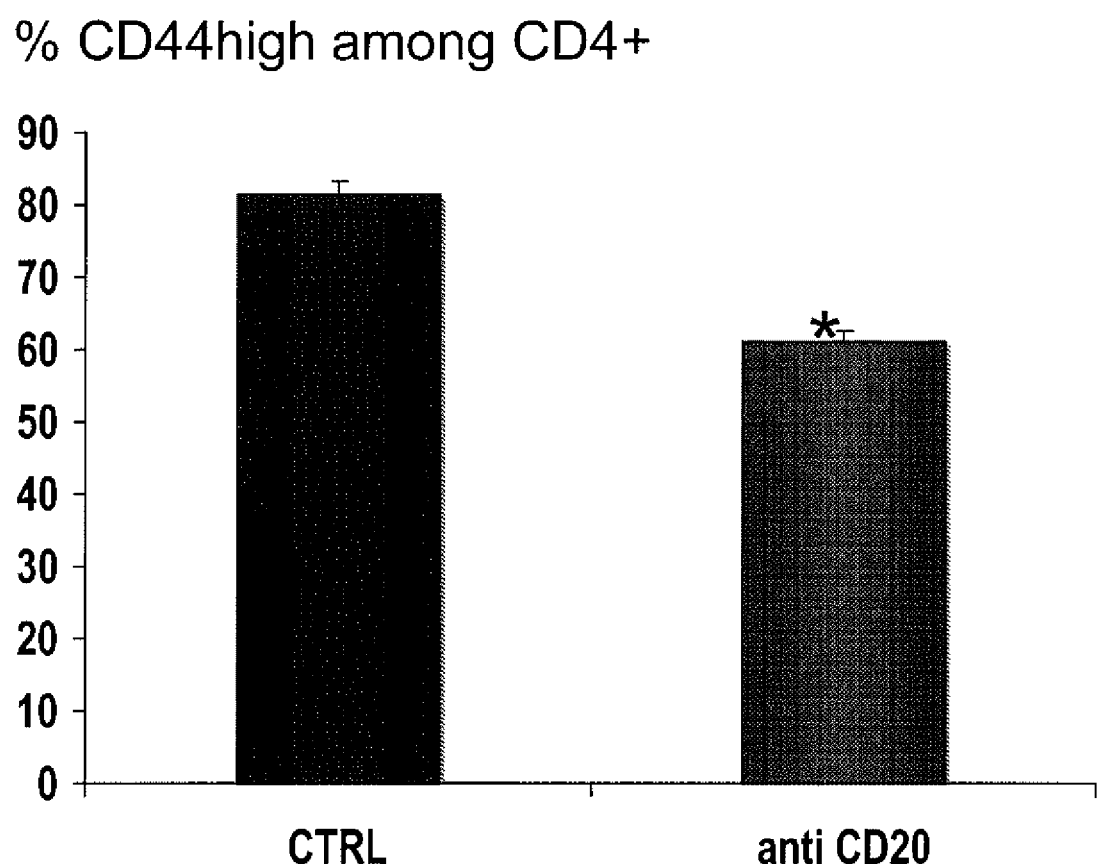
Figure 6:
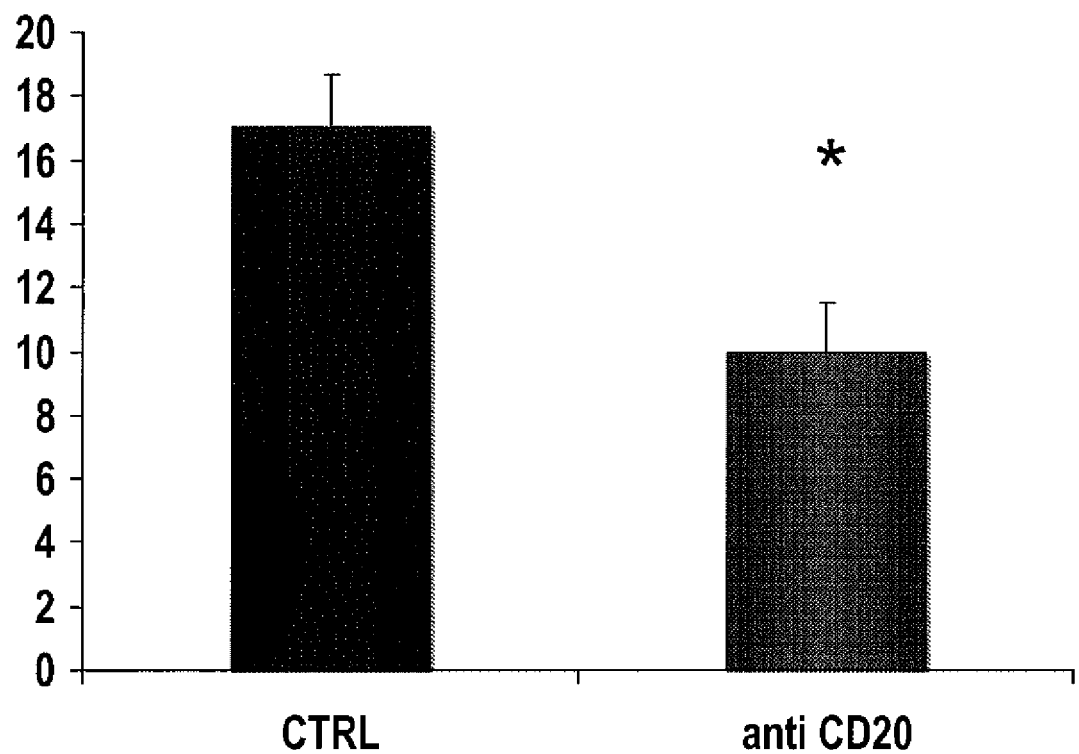

FIG. 5: B cell depletion induces a decrease of CD44 high expression by splenic CD4 T cell suggesting a CD4 T cell deactivation FIG. 6: B cell depletion induces a decrease of BrdU incorporation in vivo by splenic CD4 T cell indicating a decrease of in vivo CD4 T cell proliferation.

Figure 7:
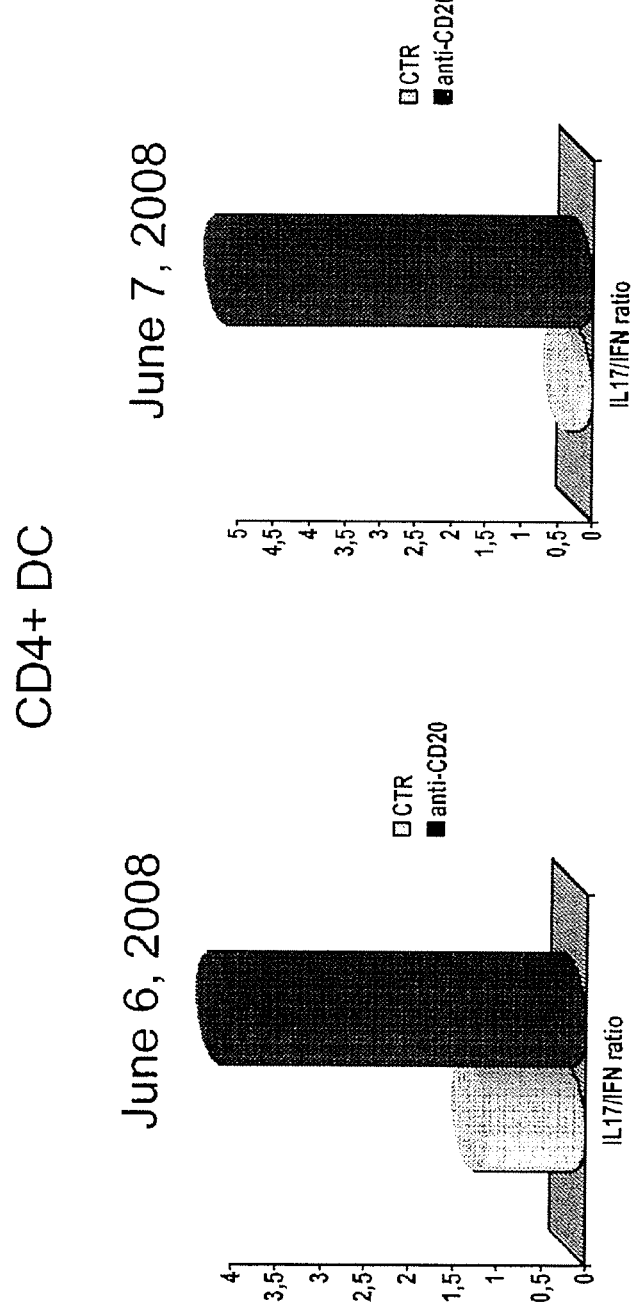
Figure 8:
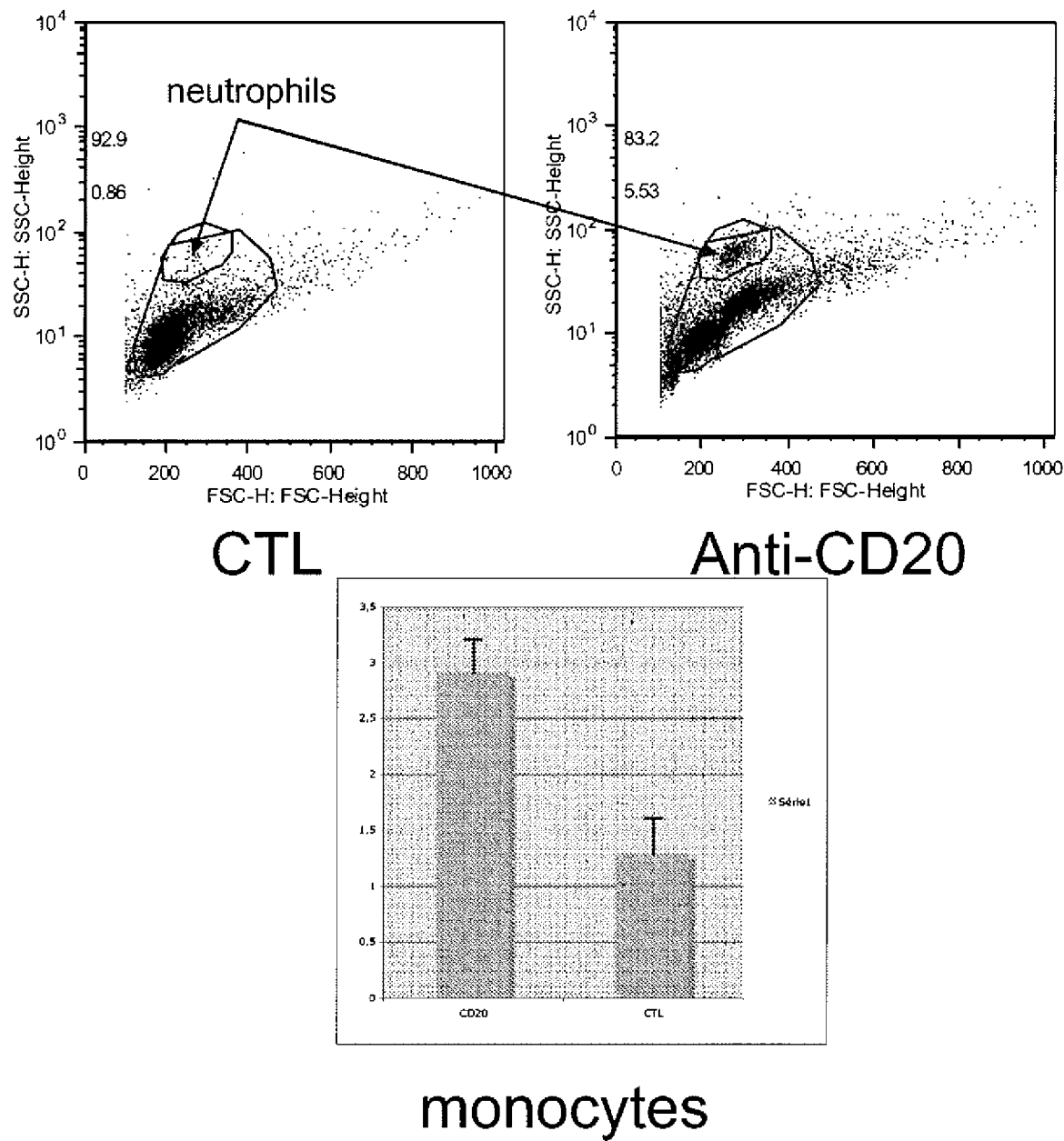

FIG. 7: Cytokine production by purified splenic CD4+ T cell stimulated in vitro with anti-CD3 antibody in the presence of purified CD11c+ dendritic cells FIG. 8: Neutrophil cell count (Ly6G+ CD11b+) and monocyte cell count (CD11b+/Ly6G−/Ly6Chigh, low or neg) was assessed using flow cytometry (First set of experiments). Inventors found increased neutrophil and monocyte cell count after 3 months of anti-CD20 treatment.

Figure 9:
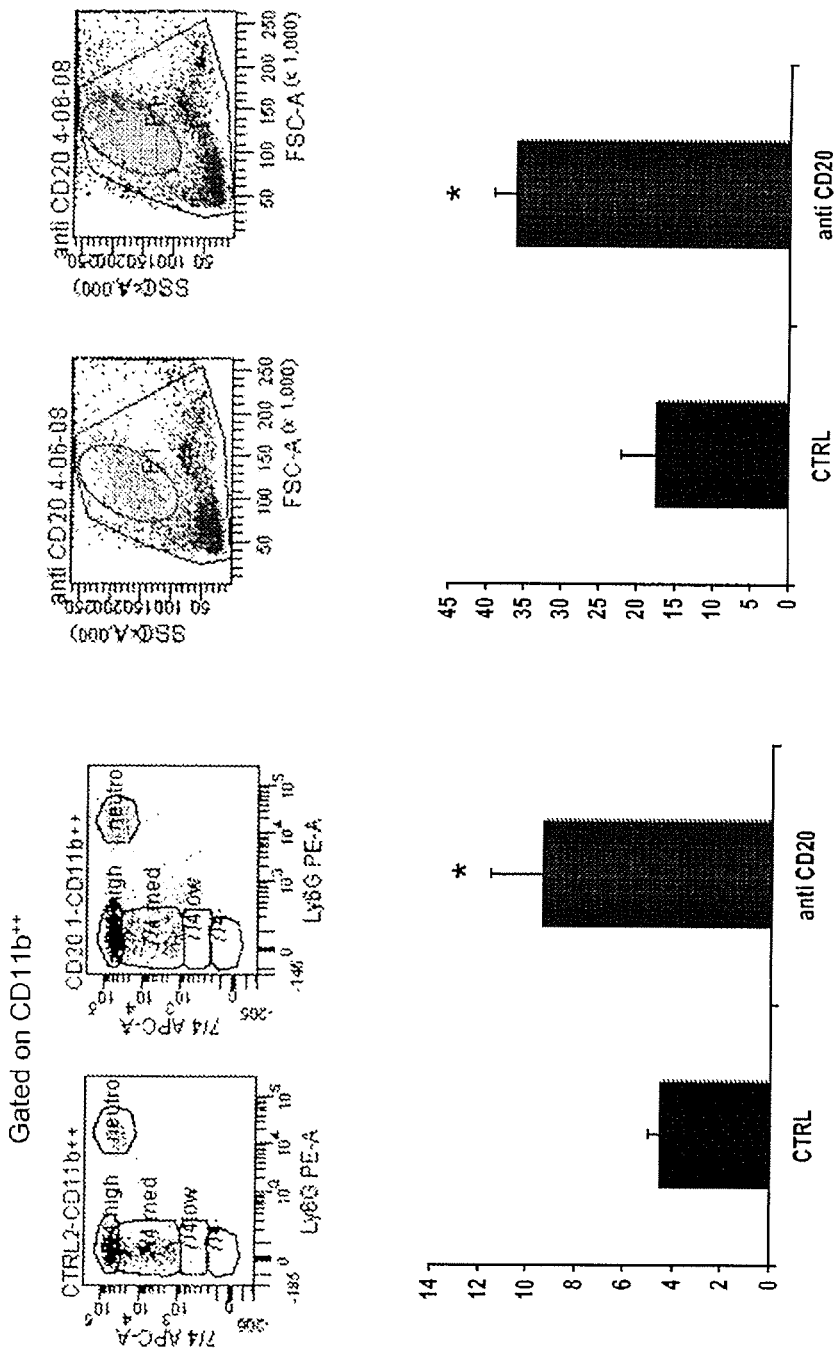

FIG. 9: Neutrophil cell count (Ly6G+ CD11b+) and monocyte cell count (CD11b+/Ly6G−/Ly6Chigh, low or neg) was assessed using flow cytometry (Second set of experiments). Inventors found increased neutrophil and monocyte cell count after 3 months of anti-CD20 treatment.

Figure 10:
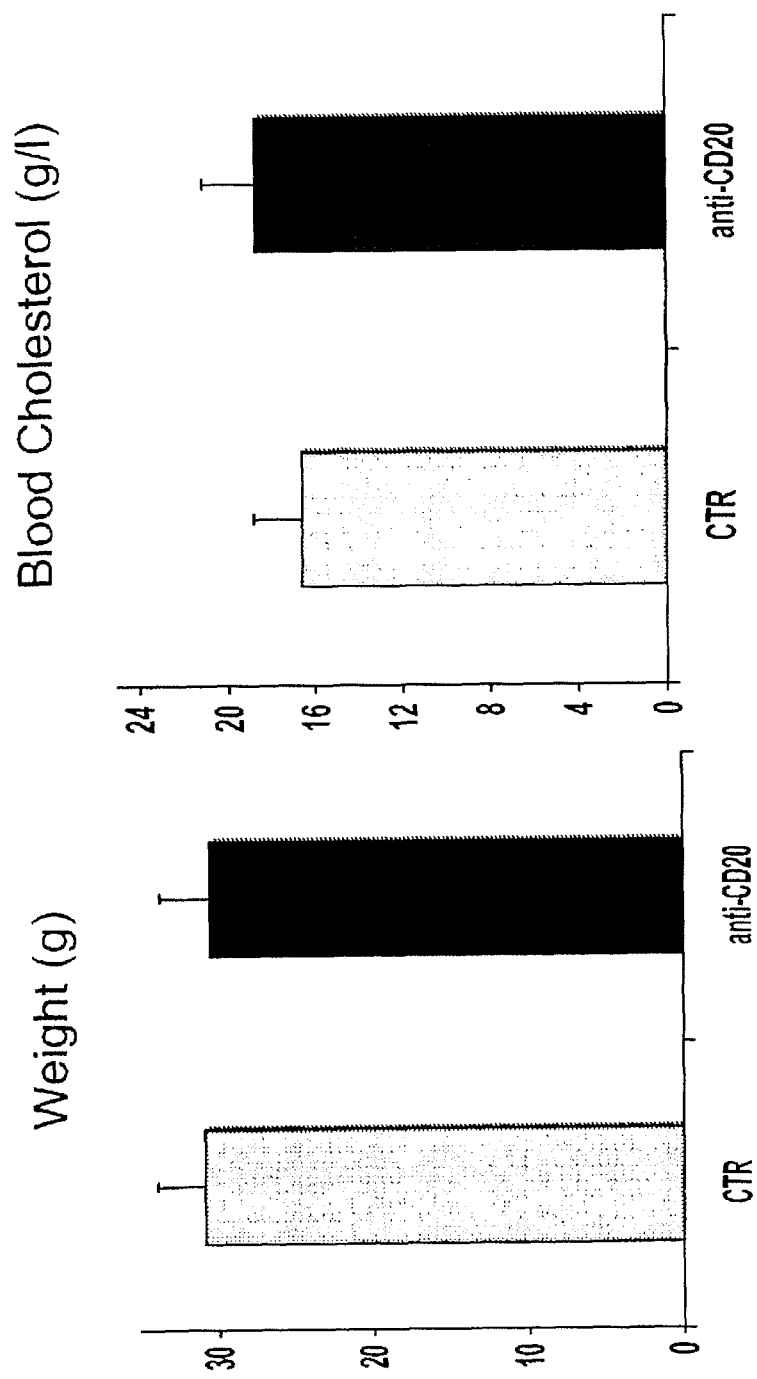

FIG. 10: Weight and plasma cholesterol levels were similar between the groups after 3 months of treatment.

Figure 11:
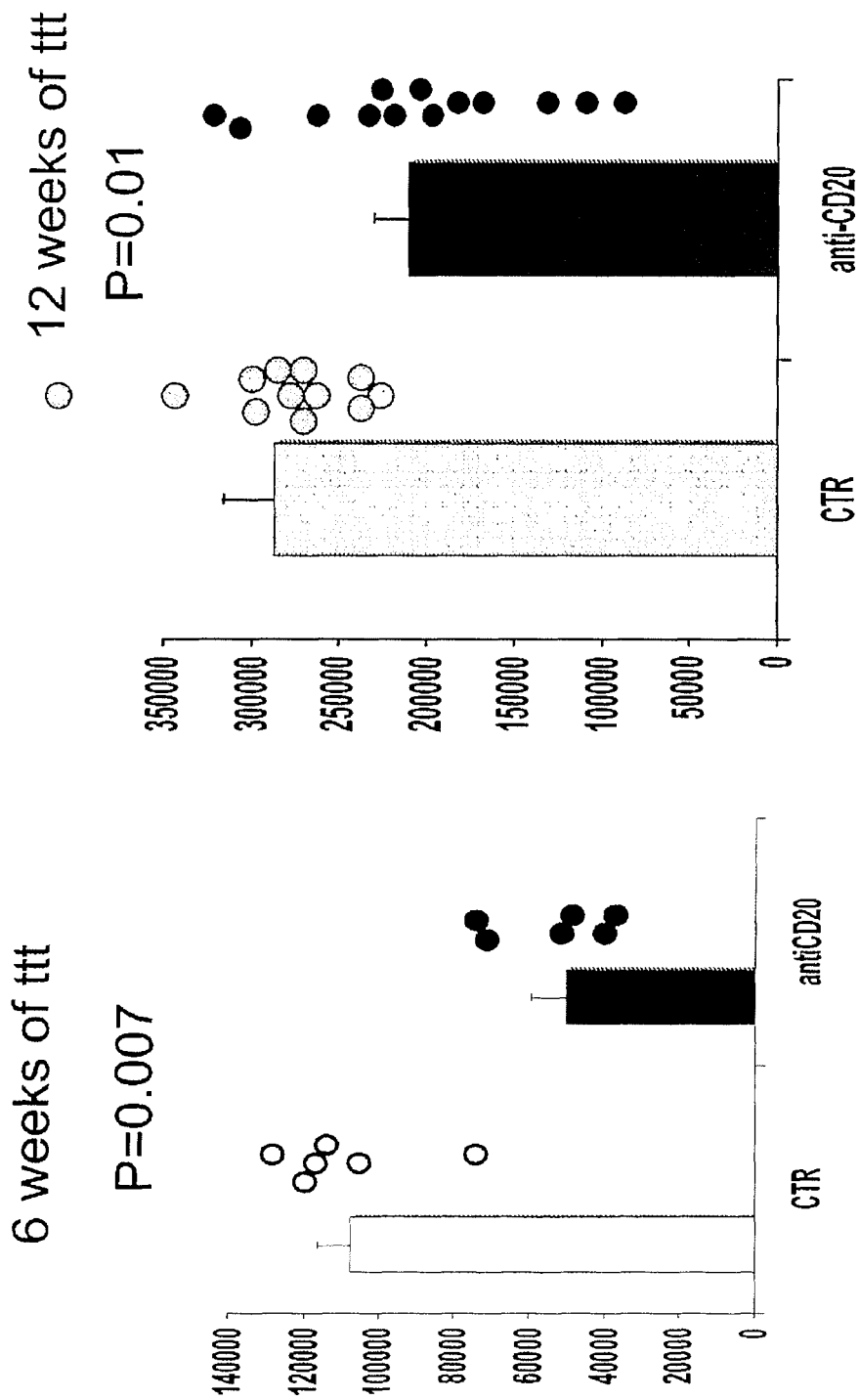

FIG. 11: Significant reduction in aortic sinus lesion size in the groups of mice treated with an anti-CD20 antibody (MB20-11) after 6 or 12 weeks of treatment.

FIG. 12A-D: CD20 mAb (α-CD20) treatment depletes B cells and reduces the development of atherosclerosis. Panels A to D show reduction of atherosclerosis development after α-CD20 therapy in 4 different experiments using Apoe~~ or Ldlr~~ mice fed either a chow diet (CD) or a western diet (WD). Representative photomicrographs of Oil red O-stained aortic sinuses are shown for each experimental setting along with quantification of intimal lesion size. Bars indicate median values.

Figure 13:
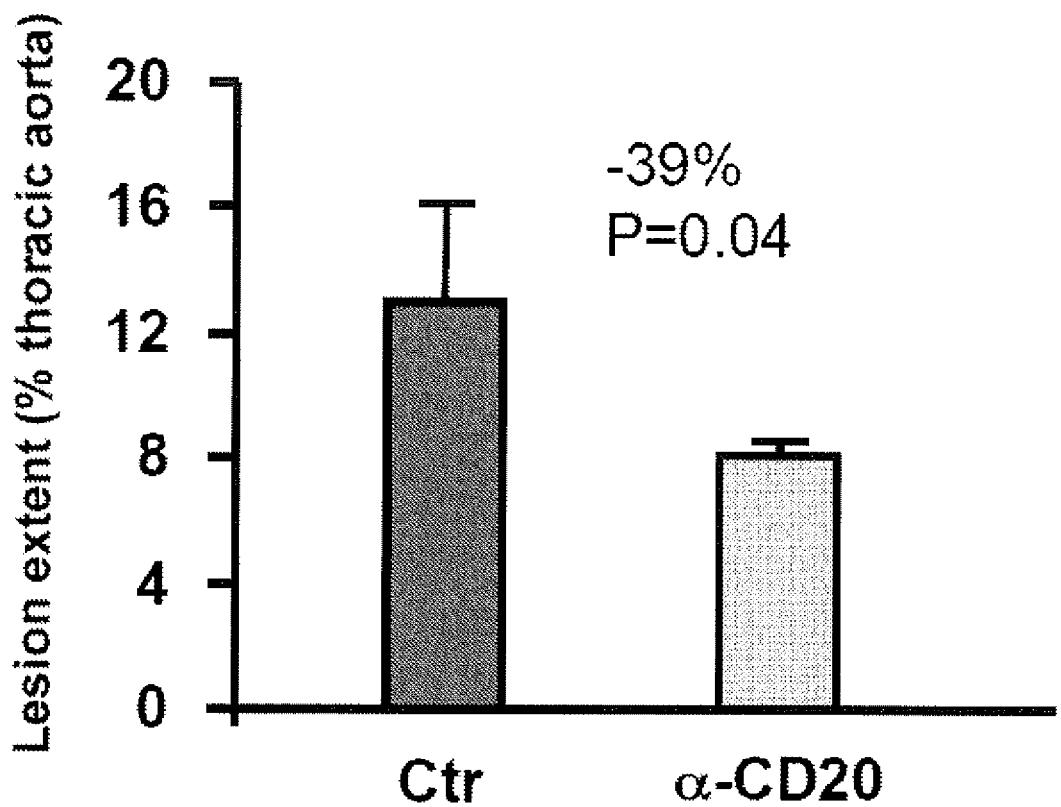

FIG. 13: CD20 mAb (α-CD20) treatment reduces the development of atherosclerosis in the thoracic aorta. Quantitative analysis of the extent of Oil red O staining in thoracic aortas Apoe" mice fed a western diet for 12 weeks and treated with α-CD20 or a control antibody. Data (mean values±s.e.m.) are representative of 9 (Ctr) to 10 mice (α-CD20) per group.

Figure 14:
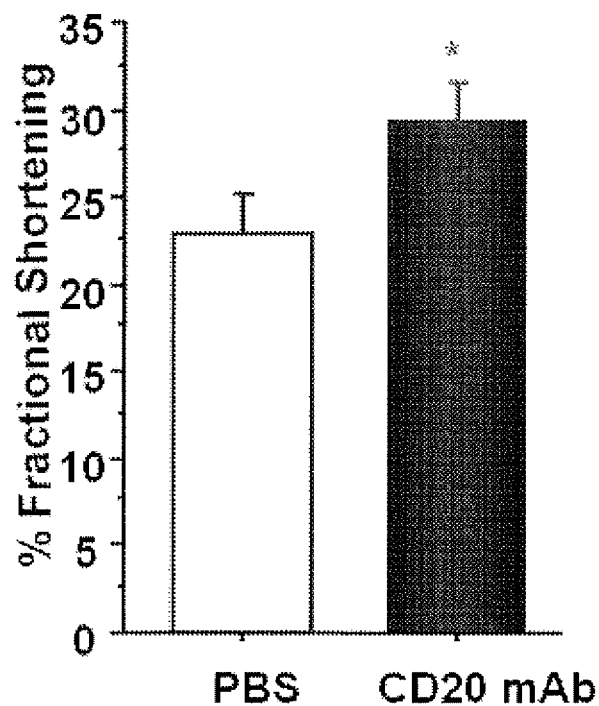

FIG. 14: B cell depletion after myocardial infarction. Quantitative cardiac function is shown.

EXAMPLE 1

B Cell Depletion and Atherosclerosis

Results and Discussion

The development of atherosclerosis is associated with signs of B cell activation, particularly manifested by enhanced production of natural IgM type and adaptive IgG types anti-oxidized low-density lipoprotein (ox-LDL) (auto) antibodies (Caligiuri et al, 2002; Shaw et al., 2000). However, in contrast to other immune-mediated diseases, i.e., rheumatoid arthritis and systemic lupus erythematosus, B cells have been assigned a protective role in atherosclerosis (Caligiuri et al., 2002; Major et al., 2002; Binder et al., 2004; Miller et al., 2008). Although IgG types anti-ox-LDL antibodies show variable association with vascular risk, circulating levels of IgM type anti-ox-LDL antibodies have been more frequently linked with reduced vascular risk in humans (Karvonen et al., 2003; Tsimikas et al., 2007). In mice, IL-5- and IL-33-mediated atheroprotective effects have been indirectly associated with specific B1 cell activation and enhanced production of natural IgM type anti-oxLDL antibodies (Binder C J et al, 2004; Miller A M et al, 2005). On the other hand, splenectomy or transfer of μMT-deficient (B cell deficient) bone marrow into lethally-irradiated atherosclerosis-susceptible mice resulted in profound reduction of IgG or total anti-oxLDL antibody production and was associated with acceleration of lesion development.

These studies led to the current paradigm that overall B cell activation is atheroprotective.

Surprisingly however, whether mature B cell depletion accelerates atherosclerotic lesion development in immunocompetent mice, as expected from previous studies, is still unexplored. This is a critical question given the potentially important risk of cardiovascular complications that might arise from the clinical use of B cell depleting CD20-targeted immune therapy in patients with severe rheumatoid arthritis or systemic lupus erythematosus, who are at particularly high risk of cardiovascular diseases.

Figure 12:
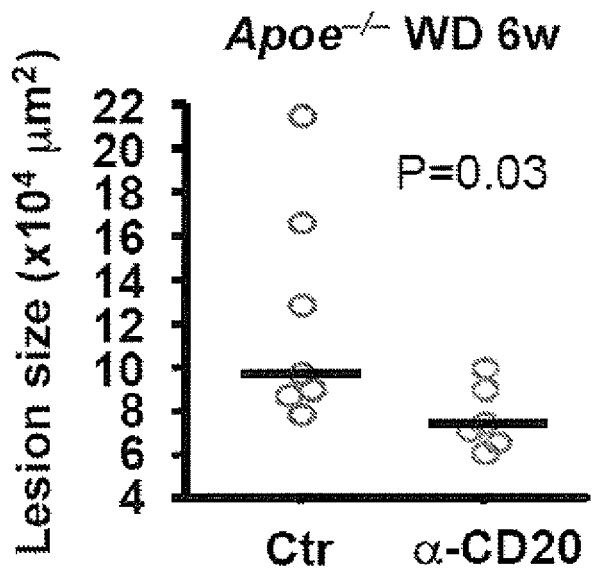
Figure 12B:
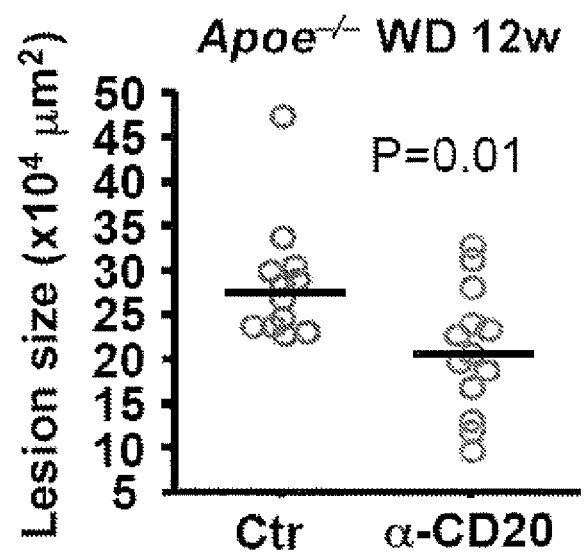
Figure 12C:
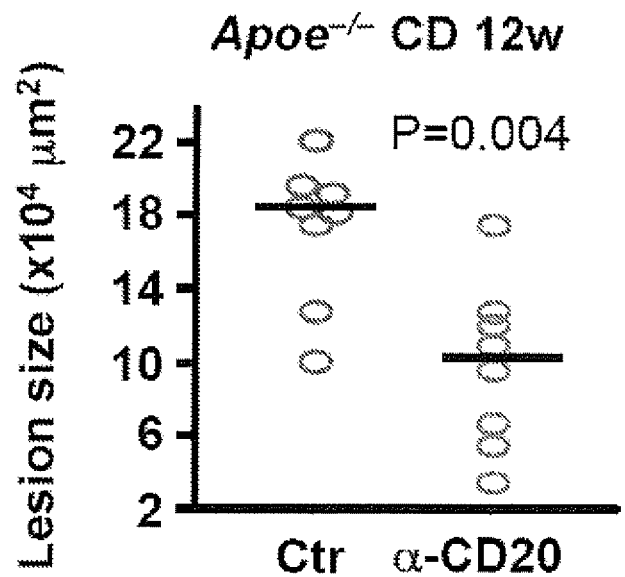
Figure 12D:
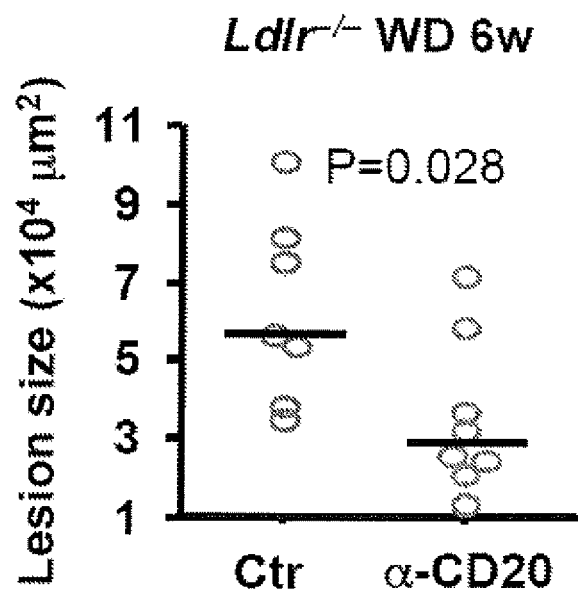

In order to directly assess the role of B cells in atherosclerosis, inventors examined lesion development in mice with or without B cell depletion. They first used $Apoe^{-/-}$ mice fed a high fat western diet, a model previously shown to be associated with significant B cell activation and high production of anti-ox-LDL antibodies, and previously used to assess the protective role of B cells in atherosclerosis. To deplete B cells, mice were treated every 3 weeks with a previously validated mouse monoclonal CD20 antibody (Uchida et al., Int Immunol, 2004; Uchida et al., *J Exp Med*, 2004) for either 6 or 12 weeks. Control mice received a control monoclonal antibody (mAb). As expected, treatment with CD20 mAb led to sustained and profound reduction of the number of mature B cells in blood (FIG. 1), spleen (FIG. 2), peritoneum and bone marrow. $B220^{high}$ $IgM^+$ cells were severely depleted (92% to 100%) at all studied sites. Spleen $B220^{low}$ $IgM^+$ cells also showed a marked reduction (~80%) but, as previously observed, immature bone marrow $B220^{low}$ ($IgM^+$) cells (FIG. 3) were less sensitive to CD20 mAb-mediated depletion. Treatment with CD20 mAb for 6 weeks did not affect plasma cholesterol levels (6.4±0.9 vs 6.3±0.8 g/L in control and CD20 mAb-treated groups, respectively, P=0.88) but unexpectedly led to a significant reduction, not acceleration, of atherosclerotic lesion development (FIG. 12A). Inventors subsequently analyzed the experiments of $Apoe^{-/-}$ mice treated for 12 weeks under high fat diet and still found a significant reduction in atherosclerosis at 2 different vascular sites (FIG. 12B and FIG. 13), despite similar plasma cholesterol levels (18.7±1.1 vs 17.9±1.0 g/L in control IgG and anti-CD20-treated groups, respectively, P=0.68). In order to rule out the possibility that the athero-protective effect of CD20 mAb treatment was due to the use of a mouse model that generates excessive inflammation in response to a very high lipid overload, the effect of B cell depletion was examined in $Apoe^{-/-}$ mice fed a chow diet. Treatment of these mice with CD20 antibody for 12 weeks also resulted in significant reduction of lesion development (FIG. 12C), despite similar plasma cholesterol levels (5.5±0.6 vs 5.7±0.8 g/L in control IgG and CD20 mAb-treated groups, respectively, P=0.96). The elevated plasma cholesterol levels in $Apoe^{-/-}$ mice are mostly of the very low-density lipoprotein (VLDL) subtype, whereas elevated LDL is the major atherosclerosis risk factor in humans. Thus, inventors examined the effects of B cell depletion in the LDL receptor-deficient ($LDLr^{-/-}$) mouse model. Again, treatment of $LDLr^{-/-}$ mice with CD20 mAb led to marked B cell depletion and to a significant reduction of atherosclerosis (FIG. 12D).

Overall, these studies provide solid evidence for an unsuspected pro-atherogenic role of B cells in three mouse models of atherosclerosis.

Inventors next addressed the potential mechanisms responsible for atheroprotection after B cell depletion. They found that treatment with CD20 depleting antibody resulted in a profound reduction of IgG type anti-oxLDL antibodies both at 6 and 12 weeks of treatment, which was consistent with the profound depletion of $B220^{high}$ cells in blood, spleen and bone marrow. It could be argued that anti-oxLDL IgG reduction might have limited the potentially deleterious consequences of immune complex formation on atherosclerosis. However, in other studies and particularly after splenectomy, profound reduction in anti-oxLDL IgG levels was observed in association with acceleration, not reduction, of atherosclerosis. Thus, in the absence of studies directly addressing the role of IgG type anti-oxLDL antibodies on atherosclerosis, changes in anti-oxLDL IgG levels following CD20 mAb treatment could not be held responsible for lesion reduction. Levels of IgM type antibodies against either copper-oxidized or malondialdehyde-modified LDL were also reduced after 6 or 12 weeks of CD20-targeted therapy. IgM type antibodies are endowed with atheroprotective properties and their reduction after CD20 mAb therapy could not account for athero-protection but instead, might have impeded the reduction of atherosclerosis. It is interesting to note, however, that IgM type anti-oxLDL and T15id+ IgM antibodies showed a much lower reduction compared to IgG type antibodies, which might have preserved an athero-protective pathway. IgM type antibodies dominate the humoral response to oxLDL in $Apoe^{-/-}$ mice and are increased even at a young age (before the initiation of CD20 mAb treatment in this study), which may explain, at least in part, the persistence of a significant IgM level after CD20 immunotherapy, a treatment that does not dramatically affect pre-existing antibodies titers. IgM persistence may also be related to the delay required to markedly deplete peritoneal B1 cells using CD20 mAb.

Inventors next examined atherosclerotic lesion composition to gain more insight into the mechanisms of atheroprotection. Interestingly, CD20 mAb treatment was associated with a significant and specific reduction of T lymphocyte accumulation within the lesions, suggesting a role for B cells in driving T cell-dependent lesion inflammation. As expected at this stage of lesion formation, very few B cells were detected within the plaques or within the adventitial layer regardless of the treatment group, suggesting that modulation of lesion T cell accumulation by CD20 mAb therapy most likely occurred as a consequence of systemic modulation of T cell function following systemic B cell depletion. In order to address this hypothesis, inventors examined T cell activation and proliferation. Interestingly, inventors consistently found marked reductions in CD69 and $CD44^{high}$ expression on spleen-derived $CD4^+$ T cells of mice treated with CD20 antibody compared with controls at both 6 weeks and 12 weeks of high fat diet, indicating reduced T cell activation. B cell depletion also led to significant reduction of in vivo BrdU staining of effector $CD4^+CD25^-$ T cells, suggesting reduced proliferation. Reduced T cell activation in CD20 mAb-treated mice was also consistent with the marked reduction of CD40 expression on $CD11c^+$ dendritic cells. Thus, a major consequence of B cell depletion using CD20 antibody is a marked reduction of T cell activation in vivo, which could potentially account for its atheroprotective effect.

T cell-derived cytokines significantly alter lesion development. Therefore, inventors examined the consequences of B cell depletion on cytokine production by purified T cells. Inventors found a marked reduction of pro-atherogenic IFN-γ by purified T cells recovered from CD20 mAb-treated mice compared with controls. Of note, this was associated with a deviation of the immune response towards a significant increase of T cell-derived IL-17A production in CD20 mAb-treated animals. Recent studies in inventor's laboratory identified an unexpected regulatory and protective role for IL-17A production in atherosclerosis. IL17A has also been shown to modulate Th1 polarization. In order to examine whether CD20 mAb-induced changes in T cell cytokine profile (reduced Th1 and increased IL17) could be responsible for CD20 mAb-dependent atheroprotection, CD20 mAb was administered to $Apoe^{-/-}$ mice (on high fat diet for 6 weeks) in the presence of control or anti-IL17A neutralizing antibody. IL17neutralization led to increased IFN-γ production in the atherosclerotic aortas and completely abrogated the athero-protective effects of CD20 mAb therapy, despite similar circulating cholesterol levels and despite no significant changes in anti-oxLDL antibodies levels.

Collectively, these results identify a hitherto unsuspected role for B cells in driving the development of atherosclerosis through modulation of T cell activation and cytokine production. Present results may seem in contrast with previous studies showing that both μMT deficiency and splenectomy accelerate atherosclerosis in mice. However, these studies did not directly address the role of mature B cell depletion on atherosclerosis in immuno-competent mice. Several other concomitant immune cell dysfunctions might have contributed to enhanced lesion development in μMT deficient animals. Furthermore, the reported limitation of atherosclerosis acceleration in splenectomized mice following reconstitution with purified B cells could have been confounded by the significant reduction of plasma cholesterol levels in B cell-reconstituted mice and could not be selectively attributed to B cells since T cell reconstitution also resulted in atheroprotection. Finally, it should be noted that although B cell depletion significantly limited lesion development in the present studies, the roles of specific subtypes of B cells in driving or controlling atherosclerosis merit further investigation. More particularly, it will be important to address the respective roles of regulatory versus non-regulatory B cells in these processes.

In conclusion, inventors provide strong evidence that mature B cell depletion reduces the development of atherosclerosis in mice. These results challenge the paradigm that overall B cell function is atheroprotective and show that a major B cell role in atherosclerosis is to drive T cell activation towards enhanced pro-atherogenic Th1 immune response and limited production of athero-protective IL-17. Although limited vascular B cell infiltration is detectable in the early stages of atherosclerosis, B cell accumulation substantially increases with time within and around advanced atherosclerotic coronary lesions and atherosclerotic abdominal aortic aneurysms, both in mice and humans, and is even prominent in vascular inflammation associated with other immune-mediated diseases. Inhibition of excessive B cell activation either through depletion or immune modulation might substantially limit vascular inflammation and atherosclerotic lesion development.

Methods

Animals. All mice were on C57Bl/6 background. $Apoe^{-/-}$ mice were 10-week-old males maintained on chow diet for 12 weeks or put on western diet (20% fat, 0.15% cholesterol, 0% cholate) for either 6 or 12 weeks. $Ldlr^{-/-}$ mice were 10-week-old males put on western diet for either 6 weeks. At 10-week-old, mice were treated intra-peritoneally (i.p.) with a previously validated mouse monoclonal CD20 antibody (Uchida et al., Int Immunol, 2004; Uchida et al., *J Exp Med*, 2004) or a control IgG (200 μg every 3 weeks), for either 6 or 12 weeks. In some experiments, mice received an i.p. injection of either purified neutralizing anti-IL-17A specific antibody (200 μg/mouse, twice per week) (Uyttenhove et al., 2006 and 2007; Wang et al., 2009) or control IgG for 6 weeks. Experiments were conducted according to the guidelines of the French veterinary guidelines and those formulated by the European Community for experimental animal use (L358-86/609EEC), and were approved by inventor's institution Inserm.

Extent and composition of atherosclerotic lesions. Quantification of lesion size and composition was performed as previously described (Taleb et al., 2007).

Cell recovery and purification, culture, proliferation and cytokine assays. $CD11c^+$ and $CD4^+$ cells were purified and processed for cell proliferation assays and cytokine production as previously described in detail (Taleb et al., 2007). IL-17 and IFN-γ productions in the supernatants were measured using specific ELISAs (BD Biosciences and R&D Systems).

Flow cytometry. APC-conjugated anti-CD3ε (145-2C11), FITC- or PE-Cy7-conjugated anti-CD4 (RM4-5), APC-conjugated anti-CD25 (PC61.5), PE-conjugated anti-CD69 (H1.2F3), APC-conjugated anti-IgM (II/41), FITC-conjugated anti-CD86 (GL1), PE-conjugated anti-CD80 (16-10A1), APC-conjugated anti-CD40 (1C10), PE-Cy7-conjugated anti-CD11c (N418), PE-Cy7-conjugated anti-CD11b (M1/70) and PE-conjugated anti-CD45R (B220)(RA3-6B2) were from eBioscience. FITC-conjugated anti-CD5 (53-7.3), biotin-conjugated anti-CD44 followed by APC-conjugated Streptavidin, APC-Cy7-conjugated anti-CD45R (B220) (RA3-6B2), APC-conjugated anti-IFNγ (XMG1.2) and PE-conjugated anti-IL17A (TC11-18H10) were from BD Biosciences. For blood staining, erythrocytes were lysed using BD FACS lysing solution (BD Biosciences). For intracellular cytokine staining, lymphocytes were stimulated in vitro with leukocyte activation cocktail (BD Biosciences) according to manufacturer's instruction for 4 hours. Surface staining was performed before permeabilization using intracellular staining kit (eBioscience). Forward scatter (FSC) and side scatter (SSC) were used to gate live cell excluding red blood cells, debris, and cell aggregates in total splenocyte, lymph node, bone marrow and peritoneum populations. Cells were analyzed using a BD CantoII or BD LSRII flow cytometer (Becton Dickinson).

Bromodeoxyuridine (BrdU) Labeling and Cell Analysis. BrdU labeling was performed as previously described (Fisson et al., 2007). Mini osmotic pumps (ALZET1007D; Charles River Laboratories), delivering 1.2 mg per day of BrdU (Sigma-Aldrich) for 7 d, were transplanted to mice subcutaneously under isoflurane anesthesia one week before sacrifice. Lymph node cells and splenocytes were stained with a PE-Cy7-conjugated anti-CD4 (RM4-5) and APC-conjugated anti-CD25 (PC61.5). BrdU detection was performed using FITC BrdU Flow kit (BD Pharmingen) according to manufacturer's instructions. Cells were analyzed using a BD CantoII or BD LSRII flow cytometer (Becton Dickinson).

Quantitative real time polymerase chain reaction. Quantitative Real time PCR was performed on an ABI prizm 7700 in triplicates. CT for GAPDH was used to normalize gene expression. Quantitative Real time PCR was performed for the following proteins: IL10, TGF-$\beta$ and IFN-$\gamma$.

Determination of circulating antibodies. Specific antibody titers to given antigens in plasma were determined by chemiluminescent ELISA as previously described (Friguet et al., 1985; Binder et al., 2003; Chou et al., 2009).

Statistical analysis. Values are expressed as means±s.e.m. Differences between values were examined using nonparametric Mann-Whitney or Kruskal-Wallis tests and were considered significant at $P<0.05$.

EXAMPLE 2

B Cell Depletion is Associated With an Increase in Fractional Shortening in a Myocardial Infarction Model Myocardial infarction was induced in 8 weeks old male C57BL6J mice by ligation of the left anterior descending coronary artery. One hour after myocardial ischemic injury mice were treated or not by intraperitoneal injection of a mouse monoclonal CD20 antibody (160 µg). Inventors showed that B cells infiltrated the infarct area. Blood B cells levels were analyzed by flow cytometry at days 1, 3, 7 and 14 after MI. The percentage of IgM+B220+–B cells was markedly reduced after CD20 antibody treatment. Mice were sacrificed at day 14 post-MI and cardiac function was measured by echocardiography (FIG. 14). Such treatment was associated with an increase in fractional shortening suggesting that said treatment may be beneficial for the treatment of myocardial infarction.

EXAMPLE 3

Effects of B Cell Depletion in Abdominal Aortic Aneurysm

First, inventors use a validated mouse model of aneurysm formation. Apoe$^{-/-}$ mice fed a chow or high fat diet develop abdominal aortic aneurysm when infused with angiotensin (Ang) II for 28 days (Daugherty A et al, 2000). This model reproduces the accumulation of inflammatory cells, including B cells, within and around the aneurysmal vessel.

For more precise results, inventors may also use a new model of aortic aneurysm with a high incidence of aneurysm rupture, described in patent application WO2009056419. The model uses Apoe+/+ or Apoe−/− mice, and associates both AngII infusion and neutralization of TGF-$\beta$ activity, two factors with a high relevance to the human disease. In this model, systemic neutralization of TGF-$\beta$ activity leads to unexpected and marked increase in the susceptibility of these mice to AngII-induced aortic aneurysm (92.5%), and to a high level of mortality from aortic dissection and rupture (65%).

B cell depletion using anti-CD20 mAb will be initiated at the time of aneurysm induction in order to assess its effect on aneurysm development. A first infusion of 200 µg i.p. is done one hour after aneurysm induction and a second two weeks after.

Mice are sacrificed after four weeks. Abdominal aortic aneurysm and immune response are assessed, an echography is done.

REFERENCES

Throughout this application, various references describe the state of the art to which this invention pertains. The disclosures of these references are hereby incorporated by reference into the present disclosure.

Binder, C. J. et al. Pneumococcal vaccination decreases atherosclerotic lesion formation: molecular mimicry between Streptococcus pneumoniae and oxidized LDL. Nat Med 9, 736-43 (2003).

Binder, C. J. et al. IL-5 links adaptive and natural immunity specific for epitopes of oxidized LDL and protects from atherosclerosis. J Clin Invest 114, 427-37 (2004).

Caligiuri, G., Nicoletti, A., Poirier, B. & Hansson, G. K. Protective immunity against atherosclerosis carried by B cells of hypercholesterolemic mice. J Clin Invest 109, 745-53 (2002).

Chou, M. Y. et al. Oxidation-specific epitopes are dominant targets of innate natural antibodies in mice and humans. J Clin Invest 119, 1335-49 (2009).

Daugherty A, Manning M W, Cassis L A. Angiotensin II promotes atherosclerotic lesions and aneurysms in apolipoprotein E-deficient mice. J Clin Invest. 2000; 105: 1605-1612.

Fisson, S. et al. Continuous activation of autoreactive CD4+ CD25+ regulatory T cells in the steady state. J Exp Med 198, 737-46 (2003).

Friguet, B., Chaffotte, A. F., Djavadi-Ohaniance, L. & Goldberg, M. E. Measurements of the true affinity constant in solution of antigen-antibody complexes by enzyme-linked immunosorbent assay. J Immunol Methods 77, 305-19 (1985).

Karvonen, J., Paivansalo, M., Kesaniemi, Y. A. & Horkko, S. Immunoglobulin M type of autoantibodies to oxidized low-density lipoprotein has an inverse relation to carotid artery atherosclerosis. Circulation 108, 2107-12 (2003).

Major, A. S., Fazio, S. & Linton, M. F. B-lymphocyte deficiency increases atherosclerosis in LDL receptor-null mice. Arterioscler Thromb Vasc Biol 22, 1892-8 (2002).

Miller, A. M. et al. IL-33 reduces the development of atherosclerosis. J Exp Med 205, 339-46 (2008).

Roman, M. J. et al. Prevalence and relation to risk factors of carotid atherosclerosis and left ventricular hypertrophy in systemic lupus erythematosus and antiphospholipid antibody syndrome. Am J Cardiol 87, 663-6, A11 (2001).

Shaw, P. X. et al. Natural antibodies with the T15 idiotype may act in atherosclerosis, apoptotic clearance, and protective immunity [see comments]. J Clin Invest 105, 1731-40 (2000).

Taleb, S. et al. Defective Leptin/Leptin Receptor Signaling Improves Regulatory T Cell Immune Response and Protects Mice From Atherosclerosis. Arterioscler Thromb Vasc Biol (2007).

Tsimikas, S. et al. Relationship of IgG and IgM autoantibodies to oxidized low density lipoprotein with coronary artery disease and cardiovascular events. J Lipid Res 48, 425-33 (2007).

Uchida, J. et al. Mouse CD20 expression and function. Int Immunol 16, 119-29 (2004).

Uchida, J. et al. The innate mononuclear phagocyte network depletes B lymphocytes through Fc receptor-dependent mechanisms during anti-CD20 antibody immunotherapy. J Exp Med 199, 1659-69 (2004).

Uyttenhove, C. & Van Snick, J. Development of an anti-IL-17A auto-vaccine that prevents experimental auto-immune encephalomyelitis. Eur J Immunol 36, 2868-74 (2006).

Uyttenhove, C., Sommereyns, C., Theate, I., Michiels, T. & Van Snick, J. Anti-IL-17A autovaccination prevents clinical and histological manifestations of experimental autoimmune encephalomyelitis. Ann N Y Acad Sci 1110, 330-6 (2007).

Wang, Y. et al. A critical unsuspected role for TGF-beta activity in the protection against aortic aneurysm formation and complications in adult mice. Under Revision (2009).

The invention claimed is:

1. A method for treating myocardial infarction by decreasing atherosclerotic plaque size in a subject in need thereof, consisting essentially of
    administering a therapeutically effective amount of an anti-human CD20 antibody to said subject, wherein said anti-human CD20 antibody depletes or destroys mature B cells or interferes with B cell functions in said subject and increases fractional shortening, and wherein the therapeutically effective amount is sufficient to decrease atherosclerotic plaque size in the subject, and wherein the myocardial infarction is a ST segment elevation myocardial infarction, and wherein the administering step is performed at 1 hour after onset of the myocardial infarction.

2. The method of claim 1, wherein said anti-human CD20 antibody is a full length anti-CD20 antibody.

3. The method of claim 1, wherein the anti-human CD20 antibody is administered daily.

4. The method of claim 3, wherein the dose of the anti-human CD20 antibody is 0.01, 0.05, 0.1 or 0.5 mg/day.

5. The method of claim 3, wherein the dose of the anti-human CD20 antibody is 500 mg/day.

6. The method of claim 3, wherein the dose of the anti-human CD20 antibody is 0.0002 mg/kg to 20 mg/kg of body weight per day.

7. A method for treating myocardial infarction in a subject in need thereof, consisting essentially of administering a sufficient quantity of an anti-human CD20 antibody to said subject at 1 hour after onset of the myocardial infarction, wherein said anti-human CD20 antibody depletes or destroys mature B cells or interferes with B cell functions in said subject and increases fractional shortening, and wherein the myocardial infarction is a ST segment elevation myocardial infarction.

8. The method of claim 7, wherein said anti-human CD20 antibody is a full length anti-CD20 antibody.

9. A method for treating myocardial infarction by reducing the percentage of IgM+B220+B cells in a subject in need thereof, consisting of
    administering a therapeutically effective amount of an anti-human CD20 antibody to said subject,
    wherein said anti-human CD20 antibody depletes or destroys IgM+B220+B cells in said subject and increases fractional shortening,
    wherein the myocardial infarction is an ST segment elevation myocardial infarction, and wherein the therapeutically effective amount is sufficient to reduce a percentage of the IgM+B220+B cells in the subject's blood at 1, 3 or 7 days after the administering step, and wherein the anti-human CD20 antibody is administered at one hour after onset of the myocardial infarction.

10. The method of claim 9, wherein the percentage of the IgM+B220+B cells in blood is reduced at 1 day after the administering step.

* * * * *